United States Patent [19]

de Rooij et al.

[11] 3,944,542
[45] Mar. 16, 1976

[54] CONVERSION OF KETOXIMES INTO LACTAMS IN ORGANIC SULFOXIDE SOLVENTS

[75] Inventors: Abraham H. de Rooij, Geleen; Jan Elmendorp, Brunssum; Willem J. Wassen, Geleen, all of Netherlands

[73] Assignee: Stamicarbon, B.V., Geleen, Netherlands

[22] Filed: Nov. 7, 1973

[21] Appl. No.: 413,435

Related U.S. Application Data

[63] Continuation-in-part of Ser. No. 252,877, May 12, 1972, abandoned.

[30] Foreign Application Priority Data
May 15, 1971   Netherlands...................... 7106705

[52] U.S. Cl. ..... 260/239.3; 260/239 A; 260/293.86; 260/326.5 FN
[51] Int. Cl.² ....................................... C07D 201/04

[58] Field of Search.... 260/239.3 A, 239 A, 293.86, 260/326.5 FN

[56] References Cited
FOREIGN PATENTS OR APPLICATIONS

| | | | |
|---|---|---|---|
| 1,029,201 | 5/1966 | United Kingdom.......... | 260/239.3 A |
| 41-16777 | 7/1966 | Japan............................ | 260/239.3 A |
| 44-20619 | 2/1969 | Japan............................ | 260/239.3 A |

*Primary Examiner*—John D. Randolph
*Assistant Examiner*—Robert T. Bond
*Attorney, Agent, or Firm*—Cushman, Darby & Cushman

[57] ABSTRACT

Organic sulfoxides such as dimethylsulfoxide are used in the transformation of alicyclic ketoximes into the corresponding lactams according to the Beckmann rearrangement in the presence of a strong acid cation exchange resin as disclosed. Thus cyclohexanone is dissolved in DMSO and contacted with a sulfonated copolymer of styrene and divinyl benzene to produce caprolactam in a continuous process.

10 Claims, 1 Drawing Figure

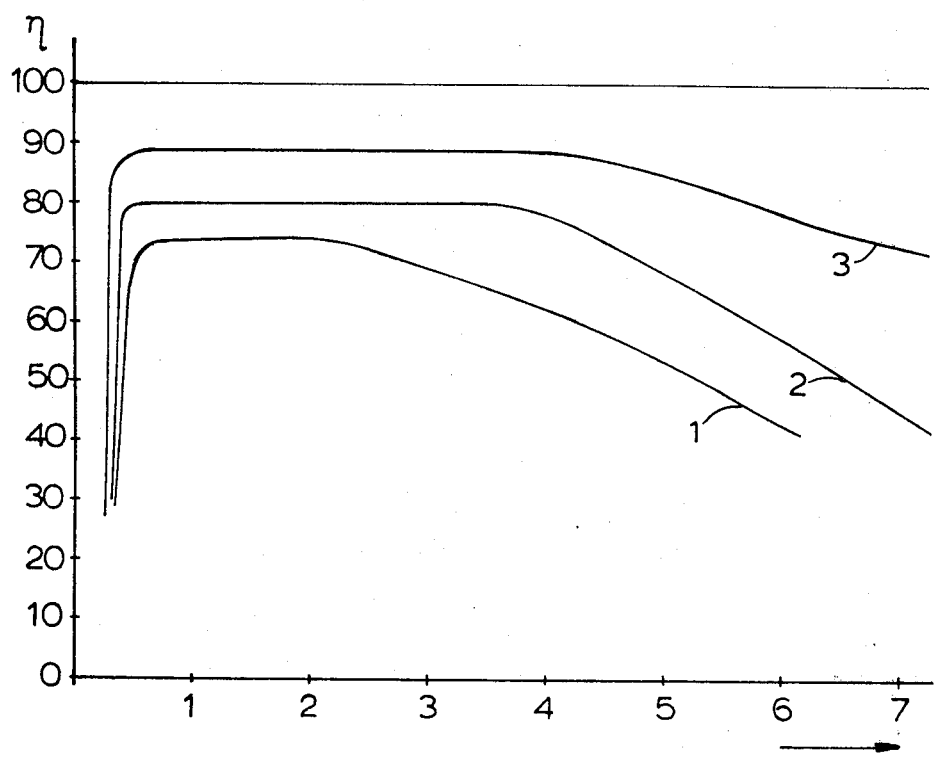

CONVERSION OF KETOXIMES INTO LACTAMS IN ORGANIC SULFOXIDE SOLVENTS

CROSS-REFERENCE TO RELATED APPLICATIONS

This is a continuation-in-part of our earlier copending application Ser. No. 252,877 filed May 12, 1972, now abandoned.

BACKGROUND OF THE INVENTION

The transformation of alicyclic ketoximes into the isomeric lactams according to the Beckmann rearrangement is usually carried out on an industrial scale, such as to form ε-caprolactam from cyclohexanone oxime, in a homogeneous strongly acid phase by means of, e.g., oleum or sulfur trioxide dissolved in liquid sulfur dioxide. The lactam-laden reaction mixture is then neutralized with ammonia water, after which the acid lactam is separated from the resulting solution of ammonium sulfate. Ammonium sulfate is subsequently recovered by crystallization from the solution that has been freed of lactam.

According to this process the preparation of ε-caprolactam is also accompanied by the production of a large amount of ammonium sulfate, often of the order of 1.7 to 1.9 tons of ammonium sulfate per ton of lactam if the conversion has been effected in oleum. Such a by-product is commercially undesirable owing to the increasing difficulties in selling ammonium sulfate, so that attempts have been made for some time to find methods of effecting the intramolecular rearrangement of oxime into lactam without by-production of ammonium sulfate.

It has already been proposed to effect this rearrangement in the gaseous phase at a high temperature in the presence of solid acid catalysts, such as boron oxide, but this method is technically and economically less attractive because the process flow, that is gases instead of liquids, occupy relatively large volumes so that the cost of apparatus and the cost of processing are high as compared with a processing in the liquid phase. Furthermore it seems that the high temperature of the process in the gaseous phase is not favorable to the quality of the resulting lactam.

It has also been proposed to effect the rearrangement under the influence of strongly acid cation exchangers in the $H^+$ form, in which process the ion exchanger comes into contact with oxime dissolved in a solvent. Cation exchangers that are mentioned as suitable for this process are sulphonated copolymers of polystyrene divinyl benzene resins, which are commercially available under the registered trade marks of "Amberlyst 15" from Rohm and Haas and "Dowex 50" from Dow Chemical.

Unlike in the rearrangement of oxime into lactam in a homogeneous medium of oleum or sulfur trioxide in liquid sulfur dioxide in which the lactam formed is liberated by neutralization of the medium with ammonia, a neutralization step of this type is omitted provided a strongly acid cation exchanger is used.

According to the process described in the British Patent Specification 1,029,201, in which cyclohexanone oxime dissolved in a reaction mixture of water-free acetic acid and acetic anhydride comes into contact with a strongly acid cation exchanger, the resulting lactam combines with the ion exchanger. The lactam can then be recovered by separating the ion exchanger and reaction liquor, washing the exchanger with water or a diluted alcohol solution and then evaporating the solvent from the lactam solution obtained. This is a multi-step process with difficulties in product and solvent recovery.

According to the process described in the Japanese Patent Publication 16,777/66, cyclohexanone oxime is brought into contact with a cation exchanger in a reaction mixture of toluene, cyclohexane, and acetic anhydride. Here the resulting lactam does not combine with the ion exchanger but remains in solution. After separation of ion exchanger and reaction liquor, lactam can be recovered from the solution by successively evaporating cyclohexane, toluene, and acetic anhydride.

In these known processes, a water-free organic acid and acid anhydride, usually acetic acid and acetic anhydride, and, in some cases, an organic solvent or mixture of solvents are always used in the reaction mixture in addition to the strongly acid cation exchanger. Depending on the circumstances the resulting lactam may combine with the ion exchanger used.

Attachment of the lactam to the ion exchanger is to be avoided. A process in which the resulting lactam combines with the ion exchanger and can be separated from the ion exchanger by a sodium hydroxide treatment is unattractive for commercialization on an industrial scale owing to the necessity of using a batch-type process; a process in which the resulting lactam remains in solution is much more favorable economically. According to such a process the ion exchanger need not be lixiviated with water to permit the recovery of the lactam and the required amount of ion exchanger will be much smaller than the stoichiometric amount required, that is an amount of 1 mole of lactam per gram equivalent of $H^+$ of the ion exchanger. In this manner the ion exchanger only serves as a catalyst for the Beckmann rearrangement and does not become loaded with lactam. The lactam that remains in solution can be recovered by distillation, but the comparatively high temperature needed to evaporate the dissolved acetic anhydride adversely affects the quality of the lactam produced.

Attempts have also been made according to Japanese Patent Publication 20,619/66 at effecting the Beckmann rearrangement with a strongly acid cation exchanger for catalyst, the oxime to be transformed being then dissolved in an organic solvent, such as benzene and toluene but, in contrast to the method described above, in the absence of an organic acid or acid anhydride. In such a process hardly any transformation appears to take place at a temperature of about 100° C, and the use of a much higher temperature e.g. above 130° C to promote the transformation is less desirable, since experience has shown that the ion exchanger cannot withstand such high temperatures.

The present invention is directed to an improved process for transforming alicyclic ketoximes, such as cyclohexanone oxime and cyclododecanone oxime, into the corresponding lactams under the influence of strongly acid solid catalyst, in particular strongly acid cation exchangers in the $H^+$ form, wherein the oxime to be transformed is dissolved in a water-free solvent. According to the disclosed process the presence of an organic acid or acid anhydride in addition to the solid acid catalyst is not needed, thereby reducing the cost of commercialization and operation.

We have found that the Beckmann rearrangement of oximes can profitably be carried out if the oxime is first dissolved in dimethyl sulfoxide (DMSO) and is then contacted with a solid strongly acid catalyst. To obtain a reasonable reaction rate, it is desirable to use a temperature in excess of 85°C but not greater than 130°C, preferably about 100° to about 120°C.

Preferably the dimethyl sulfoxide is water-free or substantially water-free. Molecular sieves may be employed to remove water from the solvent if needed.

The advantage in using dimethyl sulfoxide for the solvent is that the same solvent both activates and regenerates the solid acid catalysts, so that the catalysts can be used several times. Also the transformation of oximes into lactams by means of solid acid catalysts can be carried out by a continuous manner according to the disclosed process. The catalyst is used in a dry state, that is free from or substantially free from water to achieve best results. If the catalyst contains water it may be dried by first washing with anhydrous solvent prior to commencing the process. The catalyst may also be dried by heating.

As used herein the term solid acid catalyst indicates boron oxide or a strong-acid cation exchange resin in the H$^+$ form. These resins include the sulfonated copolymers of styrene and divinylbenzene, the active group being —$C_6H_4SO_3$ H, as recognized in the art and described in the Encyclopedia of Polymer Science and Technology, Volume 7, pages 692–704, the disclosures of which are hereby incorporated by reference. Preferred ion exchange resins have a total capacity in meg/q of about 5. The following examples refer to "Amberlyst 15," "Amberlite 200" and "Amberlite CG120" resins commercially available from Rohm & Haas Co. and "Zeroliet 227" manufactured by United Water Softeners.

The ion exchange resins disclosed herein are regenerated by treatment with 100 weight percent sulphuric acid, a solution of sulphuric acid in dimethyl sulfoxide or a solution of sulfur trioxide in concentrated sulphuric acid (oleum).

The alicyclic ketoximes to be converted according to the disclosed process have from 3 to 13 carbon atoms as does the corresponding lactam. Preferred and cyclohexanone and cyclododecanone for the commercial importance of their corresponding lactams. For example caprolactam may be polymerized according to known methods to produce nylon-6.

The conversion reaction is conveniently conducted at atmospheric pressures and, although higher and lower pressures may be used, they will generally only add to the cost of equipment, operation or both. The time required for completion or substantial completion of the transformation is subject to wide variation dependent upon the reactants, catalyst surface area and the temperature.

The process of the present invention is suited to be carried out in either a continuous or discontinuous manner. Where a continuous process is intended (see, for instance, examples 10, 11 and 12) the space velocity is maintained between 0.01 and 10 mols of oxime per liter of ion exchange resin per hour. A discontinuous or batch-type process (see examples 1–9) requires a residence time of the DMSO-Oxime solution in contact with the exchange resin catalyst of between about 10 and 120 minutes while the ratio of oxime, expressed in moles, to amount of exchange resin catalyst, expressed in gram equivalents varies from about 100:1 to about 0.1:1. Discontinuous-type processing is preferably conducted with stirring so that the exchange resin and the DMSO-Oxime solution thoroughly contact each other.

We have observed that, contrary to prior experiences of others, for instance British Patent Specification 1,029,201 mentioned above, the lactam produced according to our process does not become bound up, adhered to or combined with the exchange resin, but rather flows freely and is easily separated from the exchange resin and no special measures are required to separate the lactam from the exchange resin.

To obtain a reasonable transformation, according to known processes, it is necessary to use a reaction medium which contains, in addition to the solid acid catalyst, both a substance that apparently acts as an activator for the catalyst such as an organic acid or acid anhydride, and a substance that acts as a solvent for the lactam formed. We have found that if organic sulfoxides such as dimethyl sulfoxide are used as the solvent both functions are performed.

A further advantage for the use of dimethyl sulfoxide as solvent in the Beckmann rearrangement of oximes using a solid acid catalyst is that both higher selectivity and higher conversion efficiency are achieved as compared with those of the solvents used in prior processes. Thus we have found that, for example, at a conversion efficiency of 88 % of the oxime fed in 97 % of this oxime has been transformed into the desired lactam.

Although we do not wish to be bound by any particular theories, it appears that in the Beckmann rearrangement the dimethyl sulfoxide activates not only acid cation exchangers in the H$^+$ form, but also other solid acid catalysts such as those of the type used in the gaseous phase process of the Beckmann rearrangement, such as boron oxides, with or without a carrier, so that these solid acid catalysts can also be used in the liquid phase, in which the oxime has been dissolved in dimethyl sulfoxide.

The invention will be further described by the following example. Comparative examples are indicated by letters and are not according to the present invention, whereas examples that are according to the present invention are indicated by numbers. Unless otherwise indicated all parts and percentages are by weight.

Table I summarizes some comparative experimental results from which it appears that the use of dimethyl sulfoxide, designated as DMSO, as the solvent clearly gives better results as compared with the results obtained with other suitable solvents for oxime and lactam as disclosed in known processes.

In the following experiments a 30 % by weight solution of cyclohexanone oxime was brought into contact with the ion exchanger "Amberlyst 15" for 2 hours, while the mixture was thoroughly stirred and an $$\frac{\text{oxime (in moles)}}{\text{ion exchanger (in gram equivalents)}}$$

ratio of 4 : 1 was maintained. The amount of ecaprolactam formed has been expressed as a percentage of the amount of oxime originally present.

Table I

| example | name of solvent | formula | temperature in °C | ε-caprolactam formed |
|---|---|---|---|---|
| A | no solvent | | 110 | 3 |
| B | toluene | $C_6H_5CH_3$ | 106 | 2 |
| C | dimethyl formamide | $HCON(CH_3)_2$ | 115 | 2 |
| D | sulfolane | $(CH_2)_4SO_2$ | 118 | 0.1 |
| E | liquid sulfur dioxide | $SO_2$ | 110 (32 atm) | 1 |
| F | mixture of acetic anhydride, toluene, and cyclohexane in weight ratio of 1 : 2 : 1 | $(CH_3CO)_2O +$ $C_6H_5CH_3 + C_6H_{12}$ | 100 | 11.5 |
| 1 | DMSO | $(CH_3)_2SO$ | 110 | 40 |
| 2 | DMSO | $(CH_3)_2SO$ | 155 | 25 |

If cyclododecanone oxime is used instead of cyclohexanone oxime a 30 % conversion into laurinolactam is effected at 110° C with DMSO as a solvent under otherwise similar conditions. Similarly the formation of laurinolactam is at best only a small percent in the other solvents mentioned above.

The following table, Table II, shows that the strongly acid cation exchange resins based on sulfonated copolymers of polystyrene and divinyl resins are preferred. According to the experiments conducted relative to Table II, a 30 % by weight solution of cyclohexanone oxime in DMSO was contacted with various solid acid catalysts for about 2 hours at a temperature of about 100°C, while the mixture was stirred thoroughly.

of oxime; the ion exchanger was dried in a drying kiln at 95°C.

Example 11 in which the solvent was DMSO that had previously been dried over a molecular sieve and which contained only 0.005 % by weight, that is only 50 parts by weight of $H_2O$ per million parts by weight of solvent; the ion exchanger was dried in the same way as in Example 10. The oxime concentration was also 10 % by weight. Suitable molecular sieves are the usual synthetic zeolites e.g. type 3A manufactured by Union Carbide.

Example 12 in which the solvent was DMSO that had been dried over a molecular sieve, so that the solvent contained only 0.04 % by weight of water; the oxime concentration was 5 % by weight and the cation ex-

Table II

| example | catalyst | | temp. in °C | time in h | oxime/ catalyst ratio | ε-caprolactam formed in % by w. of oxime initially present |
|---|---|---|---|---|---|---|
| 3 | $B_2O_3$ | | 130 | 2½ | 1 : 1 (parts by weight) | 11.5 |
| 4 | $H_3BO_3 + CaHPO_4$ | strongly acid catalyst mass, as already proposed for conversion in gaseous phase | 128 | 1 | 1 : 1 | 11 |
| 5 | $H_3BO_3 + H_3PO_4 +$ $CaSO_4$ | | 130 | 1½ | 1 : 1 | 8 |
| 6 | "Amberlyst 15" | strongly acid resins with $SO_3H$ groups | 110 | 2 | 4 : 1 (mol. oxime/ equiv. $H^+$) | 30 |
| 7 | "Amberlite 200" | | 110 | 2 | 4 : 1 | 32 |
| 8 | "Amberlite CG120" | | 110 | 2 | 4 : 1 | 28 |
| 9 | "Zeroliet 227" | resin with $SO_3H$ and COOH groups | 110 | 2 | 4 : 1 | 6 |

Continuous transformations according to the present invention were carried out on a laboratory scale by passing a solution of cyclohexanone oxime in DMSO through a column filled with 40 to 45 grams of "Amberlyst 15" ion exchanger that had been carefully dried at 105°C. The height of the column was 40 cm and the internal diameter 2.5 cm.

Before the ion exchanger was introduced into the column it has been wetted with DMSO. The residence time of the oxime-containing solution in the column was 60 minutes, so that a space velocity of 1 liter of solution per liter of ion exchanger per hour was maintained. Under these conditions three experiments were carried out at 110°C as follows:

Example 10 in which the solvent is DMSO contained 0.2 % by weight of water in addition to 10 % by weight changer was freed of residual moisture by a treatment with oleum; the treatment consisted in wetting the exchanger that had been dried at 95°C first with 100 % sulfuric acid, then with oleum, again with 100 % sulfuric acid, and finally with DMSO.

The results are shown in FIG. 1 in which the lines 1, 2 and 3 are so numbered to correspond with the Examples 10, 11 and 12, respectively.

The ordinate shows the efficiency of the transformation into lactam ($\eta$) as a percentage of the amount of oxime passed through in column, and the abscissa shows the amount of solution in grams passed through as a molar ratio of cyclohexanone oxime to gram equivalent of $H^+$ of the cation exchanger.

From the figure it appears that the conversion efficiency decreases after some time, so that the cation exchanger has to be regenerated to maintain optimum conversion efficiency. As is known, strongly acid cation exchangers are usually regenerated by passing through an aqueous solution of a mineral acid such as hydrochloric acid or sulfuric acid. We have found that regeneration with an aqueous solution is not to be recommended, since it will then be necessary again to dry the regenerated exchanger thoroughly. Regeneration of the cation exchanger can now be accomplished effectively by treating the ion exchanger with 100 % by weight sulfuric acid or oleum at an ambient or slightly raised temperature such as 20–50°C, and then removing the acid by washing with the solvent to be used in the conversion. Also the ion exchanger may be treated with a solution of 10 % by weight of sulfuric acid in the solvent and then washed with the solvent only. It has been found that after such a regeneration the original capacity of the ion exchanger is restored.

Curve 3 shows that the process according to the present invention makes it possible, under water-free conditions, to obtain a conversion of 7.5 moles of oxime per gram equivalent of $H^+$ of the ion exchanger at an average transformation efficiency of 85 % before the ion exchanger has to be regenerated.

What is claimed is:

1. In the continuous process for the catalytic conversion of an alicyclic ketoxime having from 3 to 13 carbon atoms into the corresponding lactam in the presence of a solvent and a strongly acid cation exchange resin catalyst in the $H^+$ form, the improvement comprising first dissolving said ketoxime in a dimethyl sulfoxide solvent and then contacting the thus-formed solution with said exchange resin catalyst at a temperature of from about 85° to about 130° C and at a space velocity of from between 0.1 and 10 moles of said ketoxime per liter of said exchange resin per hour, thereby producing the corresponding lactam in a continuous manner free from adherence to said exchange resin and wherein said dimethyl sulfoxide solvent both activates and regenerates said exchange resin catalyst.

2. The process as claimed in claim 1 wherein the temperature of the conversion is between about 100° and about 120° C.

3. The process as claimed im claim 1 wherein the ketoxime is cyclohexanone oxime or cyclododecanone oxime.

4. The process as claimed in claim 1 wherein said ketoxime-dimethyl sulfoxide solution is passed through a column of molecular sieves thereby removing substantially all water from said solution prior to contact with said exchange resin.

5. In a process for the catalytic conversion of an alicyclic ketoxime having from 3 to 13 carbon atoms into the corresponding lactam in the presence of a solvent and a strongly acid cation exchange resin catalyst in the $H^+$ form:

the improvement comprising first dissolving said ketoxime in a dimethyl sulfoxide solvent and thereafter contacting the thus-formed solution with said exchange resin catalyst at a temperature from about 85° to about 130° C, in a ratio of ketoxime, in moles, to ion exchange resin, in gram equivalents, of between about 100:1 and 0.1:1 and for a period of contact time of the order of between about 10 and 120 minutes, thereby producing the corresponding lactam free from adherence to said exchange resin and wherein said dimethyl sulfoxide solvent both activates and regenerates said exchange resin catalyst, and thereafter removing the thus formed lactam.

6. The process as claimed in claim 5 wherein the temperature of the conversion is between about 100° and 120° C.

7. The process as claimed in claim 5 wherein the ketoxime is cyclohexanone oxime or cyclododecanone oxime.

8. The process as claimed in claim 5 wherein said ketoxime-dimethyl sulfoxide solution is passed through a column of molecular sieves thereby removing substantially all water from said solution prior to contact with said exchange resin.

9. The processes as claimed in claim 1 wherein prior to introducing said ketoxime-dimethyl sulfoxide solution the exchange resin is contacted with sulfuric acid 100 weight percent, oleum or a solution of sulfuric acid in acid organic sulfoxide, thereby regenerating the exchange resin.

10. The processes as claimed in claim 5 wherein prior to introducing said ketoxime-dimethyl sulfoxide solution the exchange resin is contacted with sulfuric acid 100 weight percent, oleum or a solution of sulfuric acid in acid organic sulfoxide, thereby regenerating the exchange resin.

* * * * *